United States Patent [19]

Hubscher

[11] Patent Number: 4,891,321

[45] Date of Patent: Jan. 2, 1990

[54] APPARATUS FOR PERFORMING DETERMINATIONS OF IMMUNE REACTANTS IN BIOLOGICAL FLUIDS

[76] Inventor: Thomas T. Hubscher, 18912 Glendower Rd., Gaithersburg, Md. 20879

[21] Appl. No.: 110,846

[22] Filed: Oct. 21, 1987

[51] Int. Cl.$^4$ .............................................. C12M 1/32
[52] U.S. Cl. .................................... 435/293; 435/292; 436/809; 436/810; 422/99; 422/102; 422/104
[58] Field of Search ............... 435/287, 292, 293, 294; 436/807, 809, 810; 422/99, 104, 102

[56] References Cited

U.S. PATENT DOCUMENTS

| | | | |
|---|---|---|---|
| 3,720,760 | 3/1973 | Rennich et al. | 436/807 X |
| 3,826,619 | 7/1974 | Bratu et el. | 436/810 X |
| 3,891,507 | 6/1975 | Breuer | 435/287 X |
| 4,135,884 | 11/1979 | Shen | 436/810 X |
| 4,155,711 | 5/1979 | Zelagin et al. | 436/531 X |
| 4,200,613 | 4/1980 | Alfrey et al. | 436/809 X |
| 4,207,289 | 6/1980 | Weiss | 422/67 X |
| 4,225,575 | 9/1980 | Piasio et al. | 436/518 |
| 4,276,259 | 6/1981 | Eibl et al. | 436/809 X |
| 4,336,337 | 6/1982 | Wallis et al. | 435/292 |
| 4,472,357 | 9/1984 | Levy et al. | 422/102 |
| 4,510,119 | 4/1985 | Hevey | 422/104 X |
| 4,591,570 | 5/1986 | Chang | 436/518 |
| 4,599,315 | 7/1986 | Terasaki et al. | 436/809 X |
| 4,643,974 | 2/1987 | Berretti et al. | 435/287 |
| 4,675,299 | 6/1987 | Witty et al. | 206/569 X |
| 4,761,378 | 8/1988 | Godsey | 436/809 X |

FOREIGN PATENT DOCUMENTS 154687 9/1985 European Pat. Off. ............ 436/809

Primary Examiner—Carl D. Price
Attorney, Agent, or Firm—Epstein, Edell & Retzer

[57] ABSTRACT

Apparatus for performing determinations of immune reactants (e.g., antigens, antibodies) in bodily fluids includes multiple test units having respective elongated rods with transversely-expanded tips at their distal ends. The tips are each coated with respective immune reactants (e.g., allergens of the type which react in a known manner with respective allergen-specific or allergen-binding antibodies in human serum. The test units are color-coded. By correlating the color code to a chart, the specific immune reactant (e.g., allergen) coating can be easily identified. The supporting strip for the test unit has through-holes which frictionally engage the proximal ends of the test unit rods with a spacing that permits all of the supported test units to be simultaneously inserted into an assembly of reaction containers arranged in a linear array. The through-hole spacing in the strip permits alternate test units to be simultaneously placed in an array of test tubes that are transversely larger than the reaction containers and supported in a linear array in a test tube rack. The tip of each test unit may take the form of two frusto-conical joined by a short cylindrical section extending longitudinally beween their larger ends. The frusto-conical sections may be multi-faceted to minimize scraping of the allergen coating from the tip during insertion and removal of the test units into the reaction containers/test tubes.

3 Claims, 3 Drawing Sheets

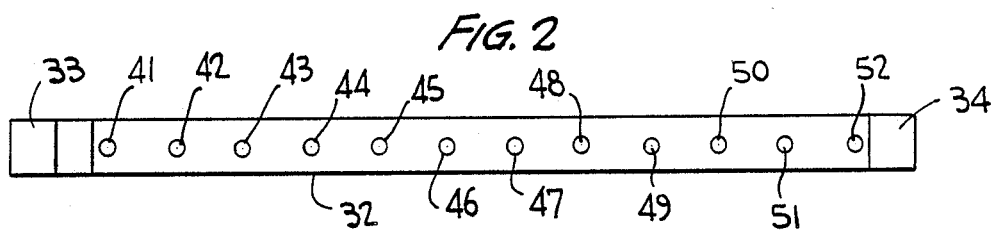
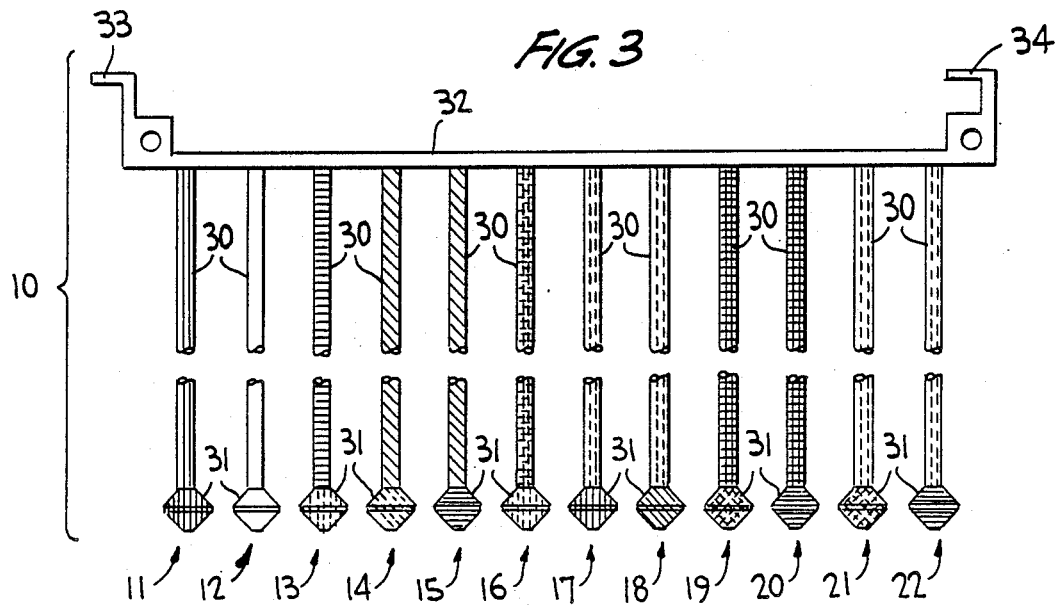
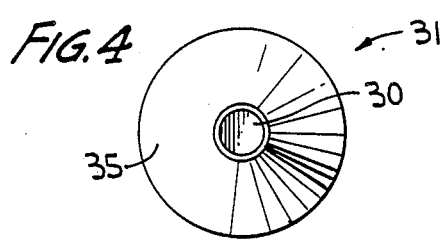
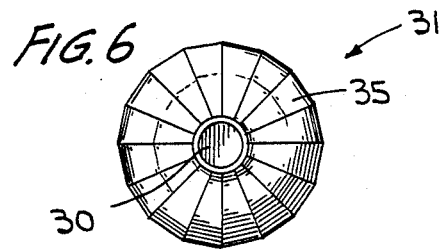
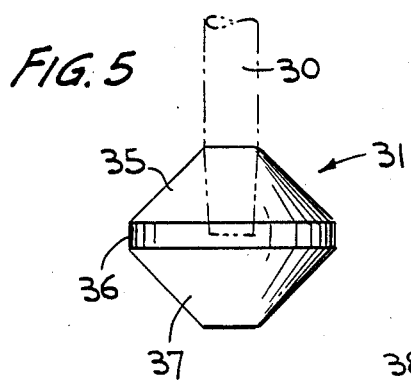
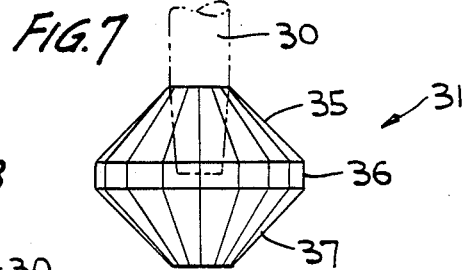
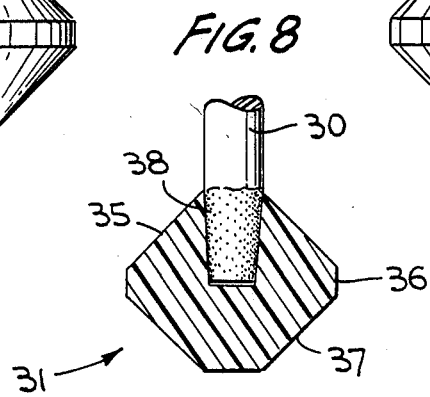

APPARATUS FOR PERFORMING DETERMINATIONS OF IMMUNE REACTANTS IN BIOLOGICAL FLUIDS

BACKGROUND OF THE INVENTION

1. Technical Field:

The present invention relates to apparatus for performing determination of immune reactants in biological fluids and, more particularly, for performing in vitro semi-quantitative determinations of allergen-specific (e.g., IgE, IgG, etc.) antibodies in human serum.

2. Discussion of the Prior Art:

It is known that, in humans, immediate type allergic reactions (e.g., hay fever, extrinsic asthma, or atopic eczema) are mediated by reaginic antibodies belonging to the IgE class of immunoglobulins. Atopic individuals exposed to allergens such as pollens, dust or animal danders, produce specific IgE antibodies against these allergens. The present invention is concerned with determining the presence of circulating allergen-specific IgE antibodies in the blood plasma or serum of an affected individual.

A technique for accomplishing this result is known in the prior art as described in (Bennich et al), U.S. Pat. No. 3,720,760 the disclosure of which is expressly incorporated herein, in its entirety, by this reference. Specifically, Bennich et al disclose an in vitro method for analyzing a test sample (e.g., a body fluid such as blood serum or blood plasma) by contacting, in vitro, the test sample with a water insoluble polymer to which a test allergen has been bound. A reaction takes place between the test allergen on the polymer and the reagin-IgE directed against the allergen so that the reagin is bound to the test allergen on the insoluble polymer. The polymer, in sheet form, and with the test allergen and the reagin-IgE attached thereto, may then be contacted with antibodies against reagin-IgE that have been labeled with a radiation-emitting atom or group. The insoluble polymer sheet is separated from the fluid, whereupon the radiation emitted from the insoluble polymer with the substances attached thereto, or the radiation emitted from the separated fluid, is measured. If the reagin-IgE directed against the allergen is present in the sample, labeled reagin is bound to the insoluble phase which then emits radiation. The latter increases with increasing concentration of the reagin-IgE in the test sample. The radiation of the liquid phase decreases with increasing concentration of the reagin-IgE as more labeled reagin is bound to the insoluble phase. The measured radiation values obtained in this procedure for the test sample can be compared with values for control samples. If instead of radioimmunoassay (RIA) techniques, one were to use enzyme-immunoassay (EIA), color intensity, rather than radiation, becomes the measured parameter.

The use of polymer sheets as a vehicle to which the test allergen is bound, and to which the allergen-specific antibodies attach, becomes unwieldy in practice. The present invention is concerned with providing apparatus that greatly simplifies the portion of the Bennich et al method during which the polymer, to which a test allergen has been bound, is inserted into the test serum to permit circulating allergen-specific IgE antibodies to attach to the bound allergen.

OBJECTS AND SUMMARY OF THE INVENTION

It is therefore a primary object of the present invention to provide apparatus for performing in vitro determinations of immune reactants in biological fluids.

It is another object of the present invention to provide a novel immunoassay kit permitting simultaneous multiple tests for respective multiple allergen-specific antibodies in human serum/plasma.

It is a more general object of the present invention to provide an improved technique for diagnosing specific allergies in humans in a manner more efficient than that described in U.S. Pat. No. 3,720,760.

It is another object of the present invention to provide a test apparatus of the type described in which multiple individual test units can be coated with respective immune reactants (e.g., allergens) and supported in a manner to permit simultaneous insertion of all the test units into appropriate reaction containers, test tubes, or the like, appropriately supported.

Yet another object of the present invention is to provide multiple test units for use in simultaneously testing blood serum, or plasma, or other body fluids, for the presence of respective allergen-specific antibodies, wherein visible indicia are used to code the test units and thereby identify the allergen coating on each test unit.

In accordance with the present invention multiple test units each take the form of an elongated rod having an allergen-coated tip at its distal end. The proximal end of each rod is frictionally engaged in a respective aperture or through-hole in a support strip so that the test units are disposed in a position-identified linear array. Spacing between the test units, as determined by the spacing between the through-holes in the support strip, matches the spacing between reaction containers in an assembly of such containers. The test unit spacing is also selected to permit alternate test units to be removed from the support strip so that the remaining test units can be inserted into respective test tubes supported in a linear array in a test tube rack.

Another important aspect of the present invention relies in the fact that color coding, or another visible indicator, is provided for the test units so that the specific allergen coating on the tip of each test unit can be readily identified. In the preferred embodiment, the color coding uses the combination of colors of the rod and tip, each combination being unique and identifying a particular allergen as indicated in a chart supplied with the system.

The tip of each test unit may take the form of two frusto-conical sections joined by a short cylindrical section disposed between their widest ends. The surfaces of the tip may be smooth; alternatively, in order to further minimize the possibility of scraping substances from the surface of the tip, the frusto-conical sections may be multi-faceted.

As part of the method for using the apparatus described above, the coated and color-coded test units, supported to depend from a support strip, are inserted into respective reaction containers containing the test serum. If there is an antibody specific to the allergen coated on any of the tips, that antibody becomes bound to the associated allergen in the corresponding reaction container. The tips are then washed, dried without rubbing, and inserted into a second set of reaction containers in which a suitable enzyme-labelled antibody conjugate has been poured. The test units are removed and rinsed once again and then placed into a third set of reaction containers containing chromogenic substrate that upon positive reaction develops a specific color. After incubation, the test units are removed (stopping the enzymatic reaction) and the remaining liquid in each reaction container is analyzed for color development and intensity by a suitable spectrophotomic analyzer such as the Micro Reader Model No. 4025 available from Dexall Biomedical Labs, Inc. of Gaithersburg, Md.

BRIEF DESCRIPTION OF THE DRAWINGS The above and still further objects, features and advantages of the present invention will become apparent upon consideration of the following detailed description of specific embodiments thereof, especially when taken in conjunction with the accompanying drawings wherein like numerals in the various figures are utilized to designate like components, and wherein:

FIG. 2 is a top view in plan of a support strip utilized in the apparatus of FIG. 1;

FIG. 3 is a front view in elevation of the support strip and test units employed in the apparatus of FIG. 1;

FIG. 4 is a bottom view in plan of one embodiment of a test unit tip constructed in accordance with the present invention;

FIG. 5 is a side view in elevation of the test unit tip of FIG. 4;

FIG. 6 is a bottom view in plan of an alternative embodiment of the test unit tip of the present invention;

FIG. 7 is a side view in elevation of the test unit tip of FIG. 6;

FIG. 8 is a sectional view of the tips illustrated in FIGS. 4 and 6 showing the manner in which the tip is secured to its supporting rod.

DESCRIPTION OF THE PREFERRED EMBODIMENTS

Figure 1:
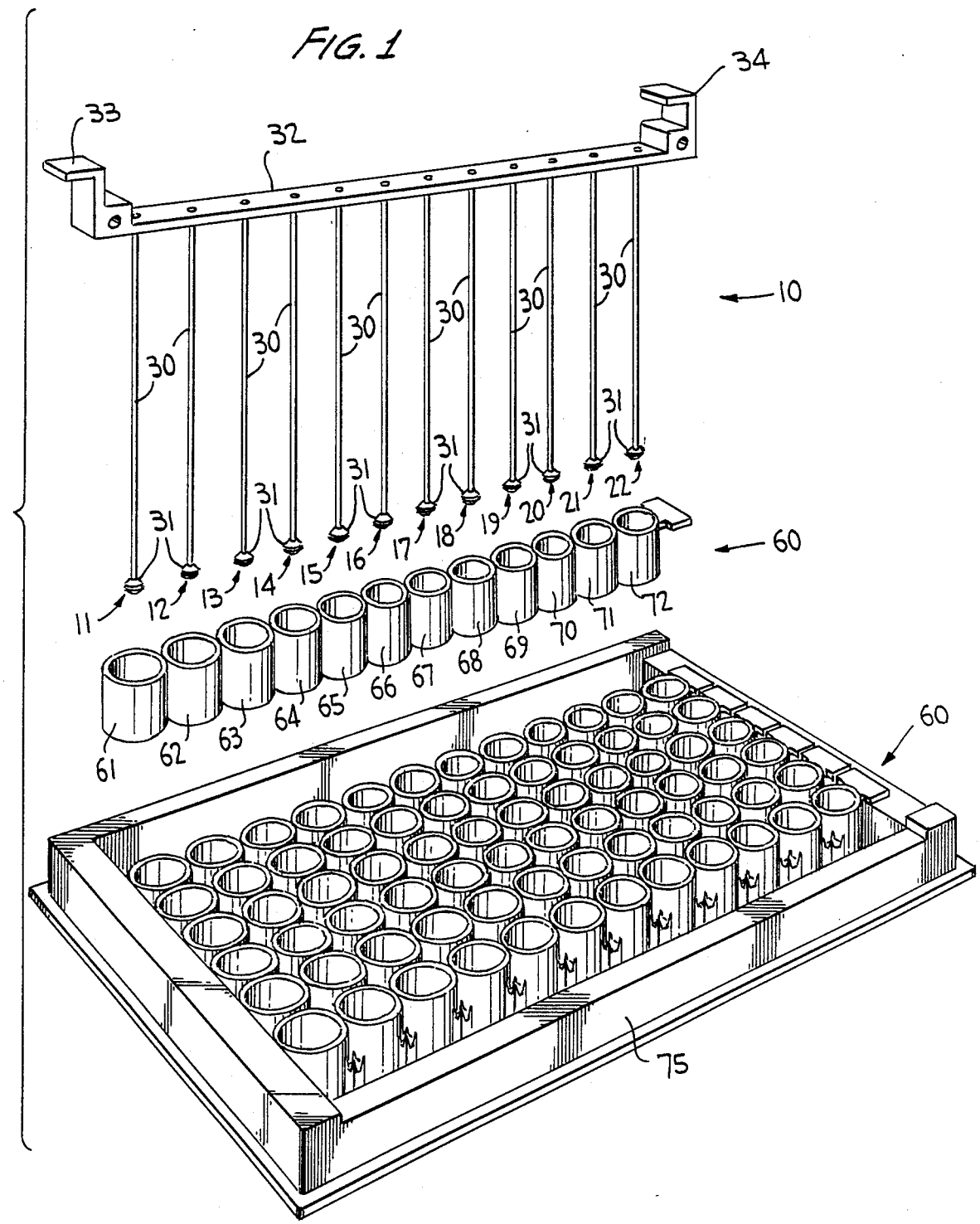
FIG. 1 is an exploded view in perspective showing one embodiment of the apparatus of the present invention.

Referring specially to FIGS. 1-8 of the accompanying drawings, testing apparatus constructed in accordance with the principles of the present invention includes an array 10 of multiple test units 11 through 22, inclusive. Although twelve test units are provided in the preferred embodiment, it is to be understood that this number is not an essential feature of the invention and that any array of three or more test units may be employed. Each test unit includes an elongated cylindrical rod 30 with a transversely expanded tip 31 secured to its distal end. Each rod 30 may be solid or hollow and has a section of reduced diameter at both its distal and proximal ends. The distal end is received in a suitable hole or aperture at the top of a respective tip 31 and is secured in place by adhesive, cement, or the like. The proximal end of the rod of each test unit 11-22 is removably engaged by a friction fit in a respective circular aperture or through-hole 41-52, inclusive, defined in an elongated holder strip 32. The substantially identical apertures 41-52 are disposed in a linear array along the length dimension of strip 32 with spaces of equal lengths between successive apertures. The apertures are positionally identified, as by molding the strip with position-identifying numbers adjacent each aperture. Alternatively, a printed gummed label may be attached to the strip to identify each aperture by position. The test units 11-22, therefore, with their rods 30 engaged in respective apertures 41-52, are supported in a linear array wherein the test units are suspended in side-by-side relation with equal spacing between each two adjacent test units. Holder strip 32 has handles/support brackets 33 34 at its opposite ends to facilitate handling/support of the strip, and the supported test units, during test procedures.

Tip 31 is required to expand to a transversely or radially larger size than the diameter of the rod 30 in order to present a large surface area for adsorbing or otherwise bonding allergen material. As illustrated in FIGS. 4 and 5, the tip 31 may take the for of three solid integrally-formed sections 35, 36 and 37. Section 35, the most proximal of the three sections, is frusto-conical with its smaller end apertured to receive the distal end of rod 30. The larger end of frusto-conical section 35 joins the axially shorter cylindrical section 36 which in turn joins the larger end of second frusto-conical section 37. The two frusto-conical sections 35 and 37 are of substantially equal axial length and identical shape but are inversely oriented axially so as to provide substantial symmetry on opposite sides of section 36. The surfaces of section 35, 36 and 37 may be smooth, as illustrated in FIGS. 4 and 5, or multi-faceted, as illustrated in FIGS. 6 and 7. In either case, the distal end of rod 30 is secured in the aperture defined in section 35 by means of suitable cement 38, adhesive, or the like, as illustrated in FIG. 8.

The test unit rod 30 and tip 31 are made of a suitable water-insoluble polymeric material that is both rigid and capable of having the described allergen materials adsorbed on, or otherwise bonded to, the tip 31. The material should be of a type which readily adsorbs the proteinaceous allergen materials. Examples of suitable polymeric materials for use in manufacturing test units 11-22 are hydrocarbon polymers such as polystyrene, polyethylene, polypropylene, polybutylene, butyl rubber and other synthetic rubbers, as well as polyesters, polyamides, vinyl and acrylic polymers such as polyvinyl chloride and polymethel methacrylate, cellulose and cellulose derivatives such as cellulose acetate. In general, any organic polymeric material which adsorbs protein in relatively large amounts will be acceptable. The preferred substrate material for the test unit is impact grade polystyrene. The coating on tips 31 is achieved by dipping the tips into the antigen/allergen solution desired and thereafter following known procedures for suitable adsorption and/or chemical bonding.

As illustrated in FIG. 1, the suspended array 10 of test units 11-22 is used in conjunction with a linear array 60 of reaction containers 61-72, respectively, formed as an integrally-molded clear plastic unit. Containers 61-72 are positioned in abutting side-by-side relation with their centers spaced by the same spacing provided between adjacent throughholes 41-52, respectively, in strip 32. Consequently, test units 11-22 may be simultaneously inserted into, or withdrawn from, respective reaction containers 61-72 by hand or automated process. To this end, the open tops of the containers are very much wider than the transverse dimension of tips 31, thereby providing adequate clearance during insertion and withdrawal. Plural arrays 60 may be supported in adjacent rows in a frame 75 so that each of the supported arrays may receive its own array of test units 11-22 simultaneously. Alternatively, different arrays 60 may be used successively in connection with the same array of test units during performance of the test procedure described below. As a further alternative, the reaction containers may be formed as one unit integrally molded with tray 75.

An important feature of the present invention is that each of the test units 11-22 in the array 10 are coded so as to be visibly identifiable and distinguishable from other test units in the same array. The coding permits a technician to correlate the visible identifier for each test unit with the particular allergen adsorbed on the tip 31 of that test unit. This is accomplished by means of a chart or table correlating each visible identifier with a corresponding allergen. The visible identifier may be the color of the tip 31, the color of rod 30, the combination of colors used for the rod and tip, a number of dots along the rod length, a number of circumferential stripes on the rod, etc. In the preferred embodiment described herein, the coded visible identifier is the color combination of the rod and tip. Typical color combinations employed for the test units are represented in Table I which is a typical example of a colorallergen correlation chart supplied with the apparatus of the present invention. The chart includes a first column listing test unit positions 11-22, a second column listing rod and tip colors for each test unit, and a third column listing the respective allergens adsorbed on each test unit tip.

TABLE I

| Test Unit | Rod/Tip Color | Allergen |
| --- | --- | --- |
| 11 | Red/Red | Blank calibrator |
| 12 | White/White | Reference calibrator |
| 13 | Blue/Purple | Oak tree |
| 14 | Green/Orange | Bermuda grass |
| 15 | Green/Blue | Kentucky blue grass |
| 16 | Yellow/Purple | Ragweed, short |
| 17 | Purple/Red | Cat epithelium |
| 18 | Purple/Green | Dog dander |
| 19 | Black/Orange | Alternaria mold |
| 20 | Black/Blue | Cladosporium mold |
| 21 | Purple/Orange | House dust |
| 22 | Purple/Blue | Dust mite (*D. Farinae*) |

The general principles of the test procedures in which the above-described apparatus is employed may be understood from the following brief description. A specific allergen, coated to a solid phase support on each tip 31, reacts with allergen-specific IgE antibodies in the patient's serum. After washing away nonspecific reactants, enzyme-labeled (peroxidase) anti-human IgE reacts with the allergen-bound human IgE. After further washing, the bound complex "allergen" - "IgE" - "peroxidase anti-human IgE is caused to react with a chromogenic substrate specific for the peroxidase enzyme. This results in the development of a green color. The intensity of the developed color is proportional to the amount of circulating allergen-specific IgE antibodies. Quantation of these antibodies is achieved spectrophotometrically, and results are expressed in standard units.

A typical test procedure using the apparatus of the present invention is set forth in the following steps:

1. For each patient serum to be tested, one array 60 of reaction containers is set in place. Each reaction container is identified as to its position (i.e., positions one through twelve).

2. One hundred microliters of a calibrator standard solution is placed in container 62 of each array 60 by means of a pipette. The calibrator standard may be a buffered and stabilized human serum solution containing a known concentration of antibodies.

3. One hundred microliters of test serum is then placed in all of the other reaction containers 61 and 63-72. It is remembered that each array 60 is dedicated to a particular patient and that only the test serum for that patient is employed in a particular array.

4. One hundred microliters of incubation medium is then placed in all reaction containers 61-72 of each array. A typical incubation medium would be a buffered protein solution containing preservatives.

5. The arrays 10 of test units, supported by respective holder strips 32, are then removed from the plastic bags in which they are supplied. Care is taken not to touch the tips 31 which are coated with specific allergen material. It is also important that the test units not be removed from the holder strip 32 until the end of the procedure.

6. Test units 11-22 are then inserted simultaneously into reaction containers 61-72, respectively. The test units may be moved up and down slightly to ensure proper mixing.

7. The inserted test units are permitted to remain in place to achieve incubation for approximately two and one-half hours at room temperature.

8. The test units, still supported by the holder strip 32, are then transferred into a rinsing dish where the test units are rinsed for at least one minute by filling the dish with distilled water. Three rinsing cycles should be performed, with all of the water drained between cycles.

9. The test units are then placed on an adsorbent paper towel with care being taken not to rub the tips 31.

10. The previously used arrays 60 are discarded and a new set of arrays 60 (one for each array 10) are set in place.

11. One hundred microliters of antibody conjugate is placed, by a pipette into each reaction container 61-72. The antibody conjugate may be an affinity purified anti-human IgE (goat) conjugated to horseradish peroxidase in a buffer with stabilizers and preservatives.

12. In addition, one hundred microliters of incubation medium is disposed by means of a pipette into each of the reaction containers 61-72. The incubation medium may be a buffered protein solution containing preservatives.

13. The test units 11-22 are gently tapped on the absorbent towel and then placed into the appropriate reaction containers 61-72 containing the antibody conjugate and incubation medium. A slight up and down motion can be applied to ensure proper mixing.

14. The inserted test units are permitted to incubate for approximately one hour at room temperature.

15. The test units are removed from the reaction containers and washed and dried by repeating steps 8 and 9 described above.

16. The just-used arrays 60 are then discarded and a new set of arrays 60 are set in place.

17. Each reaction container 61-72 receives two hundred microliters of chromogenic substrate by means of a pipette.

Figure 9:
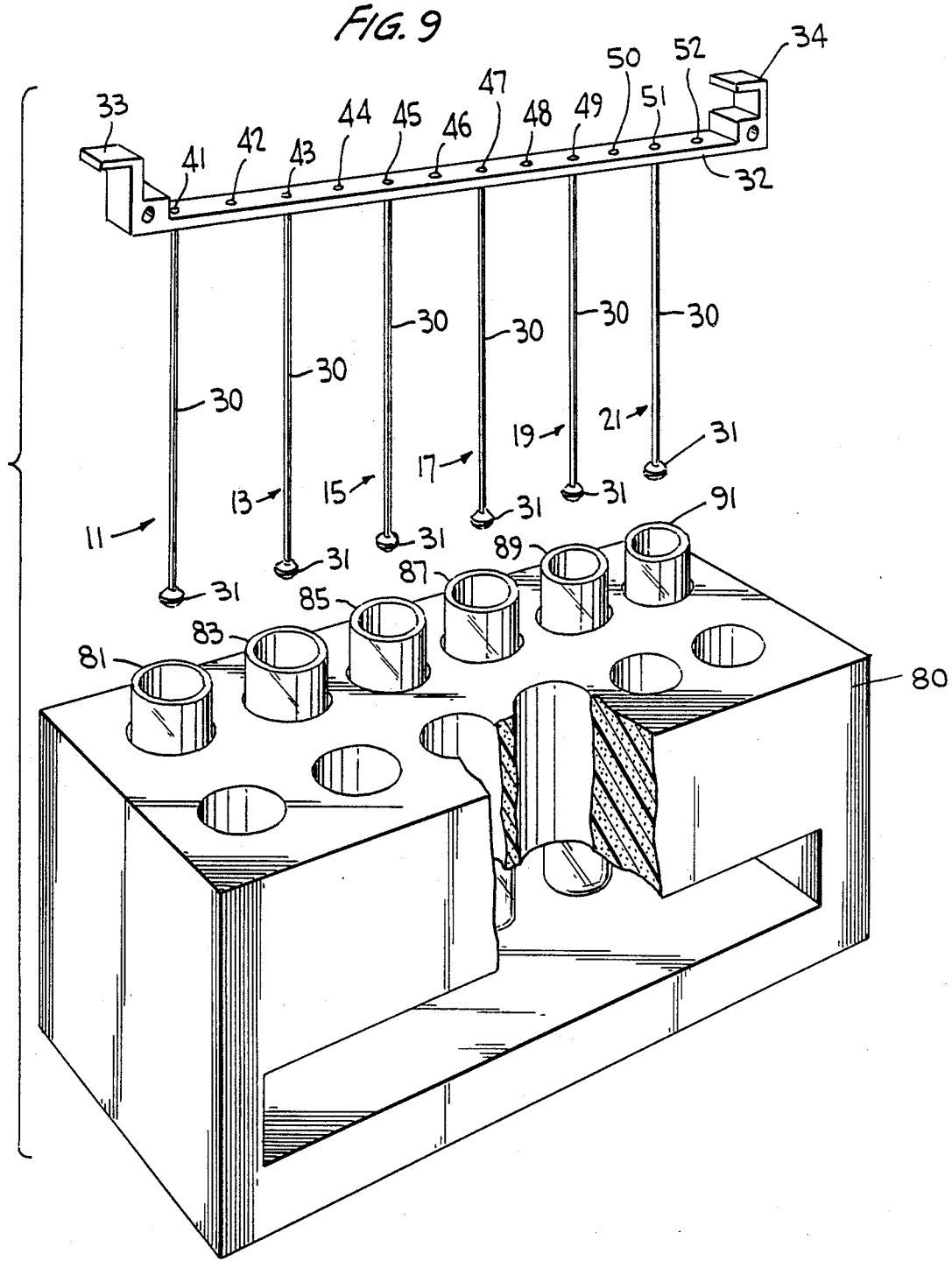
FIG. 9 is an exploded view in perspective showing how the test units and support strip of the apparatus of FIG. 1 may be employed in connection with test tubes rather than the reaction containers illustrated in FIG. 1.

18. The test units 11–22 are gently tapped on the paper towels and placed into their appropriate reaction containers 61–72, respectively, containing the chromogenic substrate.
19. Incubation is permitted to occur for thirty minutes at room temperature.
20. The test units are gently removed from the reaction containers with care being taken not to spill the contents of those containers.
21. The reaction containers of array 60 are removed from the frame 75 and placed in a micro reader such as the Micro reader model No. 4025 sold by Dexall Biomedical Labs, Inc., of Gaithersburg, Md. The results displayed by such a reader are direct concentrations of allergen-specific antibodies in the patient sera expressed in allergen units per milliliter (A.U./ml). Readings can be taken immediately or within eighteen hours, in which case the arrays of containers 61–72 should be sealed and kept refrigerated.
22. The test units may be employed with larger containers, such as test tubes, in the manner illustrated in FIG. 9. Specifically, a rack 80 for supporting test tubes 81, 83, 85, 87, 89 and 91 in a linear array has suitable supporting apertures having their centers spaced at twice the spacing between apertures defined in strip 32. In order to utilize the array of test units with the supported test tubes, alternate test units are removed from the strip 32. Thus, as illustrated in FIG. 9, the remaining test units 11, 13, 15, 17, 19 and 21 are positioned to permit their simultaneous insertion into test tubes 81, 83, 85, 87, 89 and 91. The openings of the test tubes are sufficiently wide to permit the tips of the test units to be inserted and removed without scraping.

In a typical embodiment the components of the invention described above have the following dimensions. Holder strip 32 is 4.712 inches long, 0.250 inches wide and 0.100 inches thick. The twelve apertures 41–52 have diameters of 0.062 inches and are spaced, on center, by 0.355 inches. Rods 30 are 3.375 inches long with an outside diameter at its widest point of 0.0925 inches. The proximal end of rod 30 has a reduced diameter of 0.062 inches. Tip 31 has an axial length of 0.2187 inches. Cylindrical section 36 has an axial length of 0.032 inches and an outside diameter of 0.220 inches. The frustoconical sections 35 and 37 taper at a 45° angle and are of substantially equal configuration with the exception of the rod-receiving aperture defined in section 35. That aperture extends to a depth of approximately 0.109 inches and tapers slightly at an angle of one degree in an inward direction from a diameter of 0.062 inches. The individual containers in array 60 are cylindrical and typically have an inside diameter opening of approximately 0.279 inches.

It is to be understood that the dimensions set forth above are by way of example and not limiting on the scope of the present invention.

The invention, as described in terms of the preferred embodiment, utilizes an antibody labelled with peroxidase enzyme and a chromogenic substrate specific thereto. It is to be understood, however, that this is by way of example only and not a limitation on the scope of the invention. Another example would be alkalinephosphatase enzyme with its corresponding paranitrophenyl substrate.

The invention as thus far described is specific to testing for allergen-specific antibodies in human bodily fluids. It is to be understood that the apparatus described herein, and its method of use, apply to testing other antigens, in animal and human fluids, such as bacterial, viral, or auto-antigens (i.e., lupus, DNA, etc.).

From the foregoing description it will be appreciated that the invention makes available a novel apparatus for performing determinations of allergen-specific antibodies in human serum as well as a step-by-step procedure for making such determinations.

Having described preferred embodiments of a new and improved method and apparatus for performing determinations of allergenspecific IgE antibodies in human serum in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What I claim is:

1. Apparatus for performing in vitro determinations of immune reactants, such as antigens and antibodies, in biological fluids of humans or animals, comprising:
    a plurality of test units, each test unit including an elongated rod having proximal and distal ends and a tip secured at said distal end;
    wherein said tips have different respective immune reactant coatings, each coating being of the type which reacts in a known manner with a respective corresponding immune reactive counterpart in biological fluid;
    visible coding means for distinguishing, by a visible identifier, each of said test units from all of the others of said test units; and
    holder means for supporting said plurality of test units in spaced parallel side-by-side relation;
    wherein said tips include a first multi-faceted section having a transverse configuration that expands as a function of length displacement away from proximal end, and a second multi-faceted section having a transverse configuration that contracts as a function of length displacement away from said proximal end, said second section being disposed further than said first section from said proximal end.

2. Apparatus for performing in vitro semi-quantitative determinations of allergen-specific antibodies in human serum comprising:
    a plurality of test units, each test unit including an elongated rod having proximal and distal ends and a tip secured to said distal end;
    wherein said tips have different respective allergen coatings, each allergen coating being of the type that reacts in a known manner with a respective allergen binding antibody in human serum;
    holder means for supporting said plurality of test units in spaced parallel side-by-side relation;
    wherein said tips include a first multi-faceted section having a transverse configuration that expands as a function of length away from proximal end, and a second multi-faceted section having a transverse configuration that contracts as a function of length away from said proximal end, said second section being disposed further than said first section from said proximal end.

3. Apparatus for performing in vitro determinations of immune reactants, such as antigens and antibodies, in biological fluids of humans or animals, comprising:

a plurality of test units, each test unit including an elongated rod having proximal and distal ends and a tip secured at said distal end;

wherein said tips have different respective immune reactant coatings, each coating being of the type which reacts in a known matter with a respective corresponding immune reactive counterpart in biological fluid;

visible coding means for distinguishing, by a visible identifier, each of said test units from all of the others of said test units;

holder means for supporting said plurality of test units in spaced parallel side-by-side relation;

decoding means, separate and apart from said test units, for indicating the nature of the immune reactant coating on each of said tips by correlating each immune reactant coating to a respective one of said visible identifiers;

wherein said visible identifier is the color of the test units;

wherein said holder means comprises an elongated strip having a plurality of spaced through-holes defined therein, each through-hole being sized to receive and engage the proximal end of a respective rod;

wherein said through-holes are disposed in a straight linear array with equal spacing between each pair of adjacent throughholes;

an assembly of plural reaction containers secured together and arranged side-by-side in a straight linear array, the centers of adjacent containers being equally spaced by the same spacing provided between adjacent through-holes;

wherein each reaction container has an opening that is larger in size than the largest transverse dimension of said tips to permit simultaneous insertion of said plurality of test units, suspended by said strip, into respective containers of said array; and further comprising a test tube rack having at least one linear array of openings adapted to support a respective array of test tubes, the centers of adjacent openings in said rack being spaced by twice the spacing provided between adjacent through-holes in said strip.

* * * * *